US009089527B2

(12) United States Patent
Hille et al.

(10) Patent No.: US 9,089,527 B2
(45) Date of Patent: Jul. 28, 2015

(54) TRANSDERMAL THERAPEUTIC SYSTEM COMPRISING ION PAIR MICRORESERVOIRS

(75) Inventors: Thomas Hille, Koblenz (DE); Michael Horstmann, Neuwied (DE); Walter Mueller, Andernach (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1060 days.

(21) Appl. No.: 12/515,769

(22) PCT Filed: Nov. 16, 2007

(86) PCT No.: PCT/EP2007/009926
§ 371 (c)(1),
(2), (4) Date: Dec. 14, 2009

(87) PCT Pub. No.: WO2008/061677
PCT Pub. Date: May 29, 2008

(65) Prior Publication Data
US 2010/0112064 A1    May 6, 2010

(30) Foreign Application Priority Data
Nov. 21, 2006    (DE) .......................... 10 2006 054 732

(51) Int. Cl.
| A61K 9/00 | (2006.01) |
|---|---|
| A61K 31/439 | (2006.01) |
| A61K 31/19 | (2006.01) |
| A61K 9/70 | (2006.01) |
| A61K 31/195 | (2006.01) |
| A61K 31/4164 | (2006.01) |
| A61K 31/437 | (2006.01) |
| A61K 31/4439 | (2006.01) |
| A61K 31/445 | (2006.01) |
| A61K 31/485 | (2006.01) |
| A61K 31/505 | (2006.01) |
| A61K 31/535 | (2006.01) |
| A61K 31/60 | (2006.01) |

(52) U.S. Cl.
CPC .............. *A61K 31/19* (2013.01); *A61K 9/7092* (2013.01); *A61K 31/195* (2013.01); *A61K 31/4164* (2013.01); *A61K 31/437* (2013.01); *A61K 31/445* (2013.01); *A61K 31/4439* (2013.01); *A61K 31/485* (2013.01); *A61K 31/505* (2013.01); *A61K 31/535* (2013.01); *A61K 31/60* (2013.01)

(58) Field of Classification Search
None
See application file for complete search history.

(56) References Cited

U.S. PATENT DOCUMENTS

| 4,882,163 | A | 11/1989 | Guse et al. |
|---|---|---|---|
| 6,344,211 | B1 | 2/2002 | Hille |
| 6,344,212 | B2 | 2/2002 | Reder et al. |
| 7,390,500 | B2 | 6/2008 | Mueller |
| 2003/0099695 | A1 | 5/2003 | Mueller |
| 2004/0202710 | A1 | 10/2004 | Muller |
| 2004/0234583 | A1 | 11/2004 | Muller |
| 2005/0175678 | A1 | 8/2005 | Breitenbach |
| 2005/0244485 | A1* | 11/2005 | Hsu et al. ...................... 424/448 |
| 2008/0233177 | A1 | 9/2008 | Meconi |

FOREIGN PATENT DOCUMENTS

| CA | 2 304 722 | 4/1999 | |
|---|---|---|---|
| CA | 2 370 023 | 11/2000 | |
| CA | 2 374 930 | 1/2001 | |
| CA | 2 598 353 | 9/2006 | |
| DE | 3729299 A1 * | 10/1987 | ............. A61F 13/02 |
| DE | 39 08 047 | 9/1990 | |
| DE | 198 34 005 | 4/1999 | |
| DE | 199 18 105 | 9/2000 | |
| DE | 100 12 908 | 10/2001 | |
| DE | 100 19 311 | 10/2001 | |
| DE | 101 41 651 | 3/2003 | |
| DE | 102 61 696 | 7/2004 | |
| DE | 10 2005 010 255 | 9/2006 | |
| EP | 0 305 726 | 3/1989 | |
| EP | 0 387 647 | 9/1990 | |
| EP | 0 792 145 | 9/1997 | |
| EP | 1 191 927 | 4/2002 | |
| EP | 1 731 152 | 12/2006 | |
| WO | WO 01/01967 | 1/2001 | |
| WO | WO 02/41878 | 5/2002 | |

OTHER PUBLICATIONS

Pflaster, available at http://translation.babylon.com/german/to-english/, accessed Apr. 20, 2013.*
International Preliminary Report on Patentability.

* cited by examiner

*Primary Examiner* — David J Blanchard
*Assistant Examiner* — Daniel F Coughlin
(74) *Attorney, Agent, or Firm* — Frommer Lawrence & Haug LLP

(57) ABSTRACT

The invention relates to a transdermal therapeutic system which comprises a back layer that is impermeable to the active substance, and a peelable protective layer that is impermeable to the active substance and at least one matrix layer consisting of polysiloxanes and/or polysiloxane derivatives and containing micro-reservoirs. Said micro-reservoirs contain at least one ion pair from a pharmacologically active substance and an additive and either the active substance is nucleophilic and the additive is electrophilic or the active substance is electrophilic and the additive is nucleophilic.

13 Claims, No Drawings

TRANSDERMAL THERAPEUTIC SYSTEM COMPRISING ION PAIR MICRORESERVOIRS

Transdermal therapeutic systems (TTS) have been known for a number of years. Such systems were introduced into therapy for example for active ingredients such as estradiol, norethisterone acetate, nicotine, fentanyl, tolubuterol, acetyl salicylic acid, buprenorphine and a number of other active ingredients. It is possible in this connection to divide the pharmaceutically suitable active ingredients into the group of neutral substances (norethisterone acetate, estradiol, nitroglycerin etc.), of acidic active ingredients (acetylsalicylic acid, ketoprofen, ibuprofen etc.) and in particular of basic active ingredients (nicotine, fentanyl, tolubuterol, buprenorphine, moxonidine, selegiline, salbutamol and many others).

It is intended herein that "acidic" active ingredients or compounds are to be understood as those which are electrophilic and thus can react as electron pair acceptors (anion formers), and "basic" active ingredients or compounds as those which are nucleophilic and thus can react as electron pair donors (cation formers). Examples of the former are neutral acids (e.g. HCL), cationic acids (e.g. $NH_4^+$) or anionic acids (e.g. $HCO_3^-$). Examples of basic substances are neutral bases (e.g. NH3 and organic amines), cationic bases (e.g. $NH_2-NH_3^+$) and anionic bases (e.g. $CLO_4^-$).

Transdermal therapeutic systems ordinarily have a thin and layered structure so that, with the aid of the side directly facing the skin (adhesive layer), an at least temporarily adhesive connection to the skin, through which the active ingredient is delivered, results. To improve permeation of the active ingredient through the skin, besides polymers, resins and other pharmaceutical auxiliaries, also liquid system components which are known in the narrower sense as permeation promoters are employed. Their aim is to improve the transport of active ingredient through the skin. Permeation enhancers may moreover exert their effect purely physically by improving the diffusion of the active ingredient within the pharmaceutical system, or else by simultaneously being solution improvers and, after diffusion into the skin, initiating a thermodynamic activation there (EP 1 191 927 B) or else (enhancers in the narrower sense) through a direct influence on the diffusibility in the skin by making it possible for the supply of substance to the body to be increased. Among these enhancers, it is necessary to distinguish in chemical respects a subgroup which may be described as "ion pair formers". These are in the case of the aforementioned acidic active ingredients physiologically acceptable nucleophilic basic additives such as, for example, ammonia, propylamine, tromethamol, triethanolamine and many other substances known from the literature. In the case of the more frequently employed basic active ingredients, acidic, i.e. electrophilic, additives are employed to form an ion pair, such as, for example, oleic acid, lauric acid, laevulinic acid and other fatty acids, but also aromatic acids such as benzoic acid or else sulfonic acids such as, for example, hexane sulfonic acid. Ion pairs are physicochemical molecular associations consisting of two charged molecules which form, through effective neutralization of the ionic conditions, an association which has an externally virtually neutral appearance and is thus more lipophilic. The active ingredient which is in each case part of this association is thus converted into a form which is more lipophilic, more diffusible and thus more suitable for skin permeation. Such associations may for this reason also represent the combination of two active ingredients, such as, for example, morphine and diclofenac. Numerous patent references and also some products on the market make use of this principle. Examples which should be mentioned are: EP 305 726 B and EP 792 145 B.

The difficulty of using such ion pairs within transdermal systems is in particular that both active pharmaceutical ingredients and the ion pair formers serving as additives reduce the cohesion of the basic polymers and thus may impair the adhesiveness. It is admittedly possible to remedy this by reducing both the concentration of the ion pair former (additive) and that of the active pharmaceutical ingredient. However, the thermodynamic activity, which determines the active ingredient flux, then decreases, is not fully manifested and the active ingredient flux remains low.

The present invention thus has as an object derived from this prior art the provision of a matrix for transdermal systems which comprises ion pairs of chargeable active ingredients and physiologically acceptable additives which form oppositely directed ion pairs, this matrix not having the disadvantages of inadequate active ingredient saturation or disadvantageous plasticization of the polymer base.

Irrespective of this object, silicones and silicon adhesives as basic constituents of transdermal matrices have been known for some time and are employed in particular because of their good compatibility. However, these normally have low solubilities for active ingredients with high diffusibility. Because of their unfavorable dissolving characteristics they have been employed as dispersing medium for so-called microreservoirs in which "ambiphilic" solvents are present for the active ingredient (EP 1 191 927 B). According to this publication, these ambiphilic solvents dissolve the active ingredient during storage in such a way that it does not crystallize, and, after the transdermal therapeutic system has been stuck on, they leave the matrix through migration into the skin and subsequently leave behind a supersaturation with consequently increased thermodynamic activity of the active ingredient. This publication does not relate to ion pairs and ion pair formers.

A comparable publication (DE 101 41 651 A1) relates to systems for the transdermal delivery of fentanyl and fentanyl derivatives which include silicone matrices with microreservoirs located therein, in which solvents are present as readily diffusible neutral substances such as, for example, dipropylene glycol or 1,3-butanediol. In the general description of transdermal therapeutic systems produced with these matrices there are indications that permeation enhancers can be used as further ingredients. This list includes besides glycerol esters, fatty alcohols and fatty acid esters, also fatty acids without an indication of where these are to be accommodated within the transdermal therapeutic systems and in which state of matter. The use of cationic ion pair formers and anionic ion pair formers, where one of these substances mentioned is an active pharmaceutical ingredient and the other is an additive, in aqueous microemulsions for nasal, rectal and/or transdermal administration is described in DE 39 08 047 C2.

The aforementioned prior art does not, however, solve the problem of the invention, of providing ion pairs consisting of active ingredients and complementarily charged additives with high thermodynamic activity and the least possible influence on the polymeric structure in transdermal systems which comprise at least one polymer matrix.

The solution of the problem of the invention consists of providing a transdermal therapeutic system comprising as at least one system component a matrix consisting of a polysiloxane polymer base material which comprises microreservoirs, characterized in that the active ingredient is present in the form of an ion pair consisting of a chargeable active ingredient and a contrarily chargeable physiologically acceptable additive, without the presence of solvents, in the said microreservoirs, this additive which is capable of ion pair formation being present in at least equimolar quantity.

The invention is described further in the following. Suitable active ingredient ion pairs may in principle consist of the pairing of active ingredient part which is initially in basic form, that is to say has a nucleophilic reaction, with additive part which is more acidic, that is to say has an electrophilic reaction, and is added in at least equimolar amount.

Active ingredients suitable for this purpose are for example nicotine, moxonidine, clonidine, scopolamine, atropine, buprenorphine, fentanyl, salbutamol, memantine, and many other highly active, in particular amin, active ingredients. The daily dose of particularly preferred active ingredients does not exceed 30 mg, because particular advantages result here because of the limited skin permeation. Suitable electrophilic additives for forming an ion pair are saturated and unsaturated fatty acids which are branched or unbranched unmodified or hydroxylated (ricinoleic acid, levulinic acid) or else derivatized in another way. However, aromatic compounds are also perfectly suitable as long as they also have the ability to assemble cationic ion pair complexes with active ingredients. Mention may be made here by way of example also of benzoic acid, heptanesulfonic acid, but also citric acid, tartaric acid and even inorganic acids such as phosphoric acid or hydrochloric acid. Since the efficiency of ion pair formation for favoring transdermal absorption can be achieved in a particular manner by lyophilic acids, preferred acidic additives have an octanol/buffer (pH 5.5 partition coefficient of more than 1).

In an analogous manner this invention relates to a transdermal therapeutic system that is characterized in that ion pairs of acidic, i.e. electrophilic active ingredients with the capability of anionic charging and basic, i.e. nucleophilically reacting additives with the capability of cationic charging, which are present in at least equimolar quantity, are present in the microreservoirs. Examples of acidic, i.e. electrophilically reacting active ingredients are diclofenac, ketoprofen, ibuprofen, acetylsalicylic acid, salicylic acid and many other active ingredients, with preference for those having a systemic daily dose of less than 30 mg. Suitable additives for such ion pairs are all amines, preferably diethanolamine, triethanolamine, dimethylaminoethanol, tromethamol and every other physiologically tolerated substance which is able as base to form ion pairs with anionic active ingredients.

The ion pairs of the invention are incorporated in a separate physical phase as semisolid/solid or liquid internal phase within the matrix which consists substantially of polysiloxanes. The matrix and also the internal phase with the ion pair may comprise further substances such as, for example, enhancers, plasticizers, hydrophilic or lipophilic polymers etc. However, matrices which are particularly preferred according to the invention have an internal phase consisting exclusively of the ion pair ("physical/chemical mixture" of the active ingredient and at least one ion pair former added in equimolar quantity).

The effect according to the invention, specifically the reduction in the effect on the cohesion of the surrounding silicone matrix and on the other hand the maximum increase in saturation (thermodynamic activity) of the active ingredient (active ingredient ion pair) can be achieved in this way.

The matrix of the invention can in the simplest case be furnished with a backing layer which is ordinarily impermeable to active ingredient and prevents adhesion to textiles, for which polyester materials are particularly suitable. The matrix may, if the silicone polymers used are silicone adhesives, be furnished as direct adhesion to the skin. Further solutions consist of a combination with controlling membranes, further adhesive layers or reservoir layers, as are known to the person skilled in the art.

The system of the invention can be produced in various ways, also building on numerous processes known to the person skilled in the art for producing internal phases in matrix systems. The following processes are used by way of example and preferably for the shown formulations of the invention:

Polysiloxane or polysiloxane derivative provided for the matrix external phase is in order to achieve flowability mixed with a solvent which is volatile at room temperature and is ordinarily immiscible with water in order to obtain a spreadable composition. "Anion former" and "cation former" are added and, with vigorous shearing and agitation, the increasingly finely dispersed individual particles are united to form single droplets, which uniting is attributable to a reaction of the two additions. The composition is then coated in a layer thickness appropriate for the transdermal therapeutic system onto a suitable dehesively treated sheet, and dried with application of heat so that the usually lipophilically chosen solvent is completely removed apart from traces.

A modification of this technique is based on mixing the polysiloxane or polysiloxane derivative, which is already present in solution, with a presolution of a further solvent, the active ingredient and the counter-ion former which is added in at least an equimolar quantity, after previous complete dissolution. This is followed by vigorous agitation so that the internal phase, which is added later, is homogeneously dispersed.

Production of the transdermal therapeutic systems of the invention is explained in more detail by the following examples:

EXAMPLE 1

2 g of moxonidine and 10 g of lauric acid are completely dissolved in 50 g of absolute ethanol by gentle heating. This solution is added to a previously prepared solution of 200 g of solid polysiloxane in 200 g of n-heptane and is vigorously stirred with a paddle stirrer for 10 min. The two-phase solution is coated while stirring with a layer thickness of about 50 µm onto a PET sheet surface-treated with fluoropolymer and dried at room temperature for three minutes. The product represents a matrix of the invention which is suitable for further processing to transdermal therapeutic systems.

EXAMPLE 2

The composition made in Example 1 is mixed with 50 g of micronized and crosslinked polyvinylpyrrolidone and further stirred for about five minutes. Under these conditions, an internal phase microreservoir size which is determined by the particle size of the added swellable polyvinylpyrrolidone particles forms and persists also after coating and drying which takes place in analogy to Example 1.

The invention claimed is:
1. A transdermal therapeutic system comprising:
   an active ingredient-impermeable backing layer;
   at least one matrix layer comprising:
      polysiloxanes and/or polysiloxane derivatives; and
      microreservoirs; and
   a detachable, active ingredient-impermeable protective layer;
   wherein each of the microreservoirs within the matrix form a solid, semisolid, or liquid internal phase which con- sists of a plurality of ion pairs, each ion pair consisting of one pharmacologically active ingredient and one additive;

wherein the additive is present in at least equimolar quantity; and wherein either the active ingredient is a cation former and the additive is an anion former or the active ingredient is an anion former and the additive is a cation former.

2. The transdermal therapeutic system as claimed in claim 1;

wherein ion pair is present in the form of a physicochemical molecular association.

3. The transdermal therapeutic system as claimed in claim 1;

wherein the internal phase represents at least 0.2% by weight of the matrix.

4. The transdermal therapeutic system as claimed in claim 1, further comprising:

at least one membrane layer.

5. The transdermal therapeutic system as claimed in claim 1, further comprising:

an additional adhesive layer.

6. The transdermal therapeutic system as claimed in claim 1;

wherein nicotine, moxonidine, clonidine, scopolamine, atropine, buprenorphine, fentanyl and its derivatives, salbutamol, or memantine is used as the cation-forming active ingredient.

7. The transdermal therapeutic system as claimed in claim 1;

wherein diclofenac, ketoprofen, ibuprofen, acetylsalicylic acid, or salicylic acid are used as the anion-forming active ingredient.

8. The transdermal therapeutic system as claimed in claim 1;

wherein a saturated or unsaturated fatty acid or derivative thereof is used as the anion- forming additive.

9. The transdermal therapeutic system as claimed in claim 1, wherein an amine is used as the cation-forming additive.

10. The transdermal therapeutic system as claimed in claim 9;

wherein the amine is selected from the group consisting of diethanolamine, triethanolamine, dimethylaminoethanol, and tromethanol.

11. The transdermal therapeutic system as claimed in claim 1;

wherein the matrix layer comprises permeation enhancers, plasticizers, and/or hydrophilic or lipophilic polymers.

12. The transdermal therapeutic system as claimed in claim 1;

wherein each ion pair is present in the form of a physicochemical molecular association;

wherein the internal phase represents at least 0.2% by weight of the matrix; and wherein the transdermal therapeutic system comprises at least one membrane layer.

13. The transdermal therapeutic system as claimed in claim 1;

wherein the at least one matrix layer consists of
the polysiloxanes and/or polysiloxane derivatives; and
the microreservoirs.

\* \* \* \* \*